United States Patent
Kim et al.

(10) Patent No.: US 8,844,138 B2
(45) Date of Patent: Sep. 30, 2014

(54) METHOD FOR MANUFACTURING DENTAL PROSTHESIS

(75) Inventors: Jae Doc Kim, Yongin-Si (KR); Yeong Kyun Kim, Yongin-Si (KR); Sung Kuk Kim, Yongin-Si (KR); Heon Joo Kim, Yongin-Si (KR); Jae Yun Park, Yongin-Si (KR)

(73) Assignee: Vatech. Co., Ltd., Yongin-Si (KR)

( * ) Notice: Subject to any disclaimer, the term of this patent is extended or adjusted under 35 U.S.C. 154(b) by 1442 days.

(21) Appl. No.: 12/449,637

(22) PCT Filed: Jul. 31, 2008

(86) PCT No.: PCT/KR2008/004460
§ 371 (c)(1),
(2), (4) Date: Aug. 19, 2009

(87) PCT Pub. No.: WO2010/002058
PCT Pub. Date: Jan. 7, 2010

(65) Prior Publication Data
US 2011/0179630 A1    Jul. 28, 2011

(30) Foreign Application Priority Data

Jul. 1, 2008  (KR) .................. 10-2008-0063639

(51) Int. Cl.
A61C 5/10         (2006.01)
A61C 13/00      (2006.01)
A61C 13/12      (2006.01)

(52) U.S. Cl.
CPC .............. *A61C 13/12* (2013.01); *A61C 13/0019* (2013.01); *A61C 2201/007* (2013.01); *A61C 13/0004* (2013.01)
USPC ....................... 29/896.1; 29/28; 29/36; 29/40

(58) Field of Classification Search
CPC .......... B23P 15/32; B23B 3/161; B23B 3/164; B23Q 39/02; B23Q 16/102; A61C 5/023; A61C 13/0003
USPC .......... 29/896.1, 896.11, 557, 558, 36, 39, 40, 29/50, 33 J, 27 C, 27 R, 28; 82/120, 121, 82/159, 129; 409/192, 203, 213, 217, 409/165–167; 451/246, 362
See application file for complete search history.

(56) References Cited

U.S. PATENT DOCUMENTS

| | | |
|---|---|---|
| 4,663,720 A | 5/1987 | Duret et al. |
| 5,224,049 A | 6/1993 | Mushabac |
| 7,112,065 B2 | 9/2006 | Kopelman et al. |
| 7,204,032 B2 | 4/2007 | Matsuda et al. |

FOREIGN PATENT DOCUMENTS

| | | | | |
|---|---|---|---|---|
| DE | 4030175 A1 | * | 3/1992 | ............. B23Q 15/22 |
| JP | 2002-224142 A | | 8/2002 | |
| KR | 2000-0060365 A | | 10/2000 | |
| KR | 10-2001-0026892 A | | 4/2001 | |
| KR | 10-0760073 B1 | | 9/2007 | |

OTHER PUBLICATIONS
Machine Translation of DE 4030175 A1; Fornoff; Mar. 1992.*

* cited by examiner

*Primary Examiner* — Ryan J Walters
(74) *Attorney, Agent, or Firm* — Stein IP, LLC

(57) ABSTRACT

A method for manufacturing a dental prosthesis is disclosed. The method includes a first step of photographing a patient's mouth with a dental cone beam CT, a second step of converting CT data photographed at the first step into a CAD file, a third step of designing a shape of the dental prosthesis with the CAD file using CAD software, a fourth step of correcting the shape of the designed prosthesis using occlusion simulation software, a fifth step of converting the shape of the prosthesis which is designed finally into manufacturing data, and a sixth step of transmitting the manufacturing data to a dental prosthesis manufacturing machine, thus manufacturing the dental prosthesis.

6 Claims, 3 Drawing Sheets

METHOD FOR MANUFACTURING DENTAL PROSTHESIS

This is a National Phase Application filed under 35 U.S.C. 371 as a national stage of PCT/KR2008/004460, with the filing date of Jul. 31, 2008, an application claiming priority benefit from Korean Patent Application No. 10-2008-0063639, filed Jul. 1, 2008, the entire content of each of which is hereby incorporated by reference in its entirety.

TECHNICAL FIELD

The present invention relates, in general, to a method for manufacturing a dental prosthesis and, more particularly, to a method for manufacturing a dental prosthesis, including the steps of photographing a patient's mouth, converting the information of the photograph into a CAD file, designing the shape of the dental prosthesis using the CAD file, converting the designed shape into data to be used for the manufacture of the prosthesis, and transmitting the manufacturing data to a dental prosthesis manufacturing machine.

BACKGROUND ART

When a tooth must be extracted because of external injury or dental caries, a dental prosthesis is used to appropriately support the inter-dental papilla or gingiva. The dental prosthesis is referred to as an artificial tooth or a false tooth. Further, the dental prosthesis means an artificial substitute for a missing natural tooth or tissue associated therewith.

The dental prosthesis has been essentially used to prevent a tooth adjacent to an extracted tooth from moving to an abnormal location during dental treatment. Particularly, in the case of a patient of a low age group or a patient who suffers from a serious periodontal disease, the dental prosthesis is utilized for maintaining occlusion properly stable.

However, when the dental prosthesis is manufactured, a high degree of accuracy is required. The dental prosthesis must be well made so as to healthily maintain the gingiva at its original position during prosthetic treatment. In order to enhance the accuracy of a final prosthesis, the gingiva must be kept healthy during the prosthetic treatment.

There are two methods which are used to manufacture the conventional dental prosthesis. That is, the dental prosthesis may be manufactured in a dental laboratory upon the order of a dentist, or may be manufactured in the care unit of a dental clinic.

In the first of the two cited manufacturing methods, the dental clinic transmits an impression to the dental laboratory. In the dental laboratory, plaster is poured into the impression, thus producing a plaster model. Next, the gingiva portion of a missing tooth is removed from the plaster model using a rotary tool. Thereafter, wax is applied to the undercut portion of the plaster model, thus correcting an abutment. The missing tooth is restored using self curing resin. Once the resin is hardened, the plaster model is discarded and the external appearance of a tooth is formed. As such, after the prosthesis has been implanted using an elastic or non-elastic material, the convalescence of a patient has been observed for several days or months. Thereafter, a semi-permanent prosthesis using ceramic or alloy is replaced.

According to the second example, after a tooth structure which had suffered the external injury or dental caries is eliminated in the clinic, the operation of spacing the peripheral rim of the eliminated tooth from the gingiva is conducted, and a dental stem directly puts the self curing resin in the mouth by hand. Next, after the resin has hardened, it is pulled out from the mouth and the external appearance of the tooth is formed using the rotary tool, so that a dental prosthesis is finished. However, when the dental prosthesis requires casting or plastic work, so that it is impossible to manufacture the dental prosthesis in the clinic, the manufacture of the dental prosthesis is entrusted to the dental laboratory.

However, the methods of manufacturing a dental prosthesis using the above-mentioned processes are problematic in that manufacturing steps are complicated, dust may be generated while the external shape is being formed, thus leading to the contamination of the clinic, and those skilled in the art are required, and manufacturing period and cost are increased.

DISCLOSURE

Technical Problem

Accordingly, an object of the present invention is to provide a method for manufacturing a dental prosthesis, which overcomes the above problems occurring in the prior art and solves technical problems lying therein.

Another object of the present invention is to provide a method for manufacturing a dental prosthesis, which solves problems occurring when a conventional dental prosthesis is manufactured through manual operation, thus reducing manufacturing period and cost.

Technical Solution

In order to accomplish the above objects, the present invention provides a method for manufacturing a dental prosthesis, including a first step of photographing the mouth with a dental cone beam CT, a second step of converting CT data photographed at the first step into a CAD file, a third step of designing a shape of the dental prosthesis with the CAD file using CAD software, a fourth step of correcting the shape of the designed dental prosthesis using occlusion simulation software, a fifth step of converting the shape of the dental prosthesis which is designed finally into manufacturing data, and a sixth step of transmitting the manufacturing data to a dental prosthesis manufacturing machine, thus manufacturing the dental prosthesis.

In order to obtain data on the patient's mouth, the patient's mouth is photographed using a dental cone beam CT. CT data which was photographed is converted into a CAD file, thus designing the anatomical and functional shape of the dental prosthesis. Thereafter, the completed design of the prosthesis is converted into prosthesis manufacturing data and transmitted to the dental prosthesis manufacturing machine, thus manufacturing a dental prosthesis.

Thus, when the method of this invention is compared with the conventional method, the dental prosthesis is manufactured by converting photographed data and operating a prosthesis manufacturing machine in response to the converted data without manual operation, thus reducing manufacturing period and cost, preventing the generation of toxic substances, contamination resulting from dust during the manufacture, and eliminating the dangers of casting, simplifying a manufacturing process, and achieving a dental prosthesis of uniform and precise quality.

After the outer surface of the dental prosthesis manufactured through the above method goes through a planning process and a sterilizing and washing process, the dental prosthesis may be put in the patient's mouth, thus appropriately supporting the inter-dental papilla or gingiva.

According to an aspect of this invention, the dental prosthesis manufacturing machine may include first and second spindles each having a roughing tool and a finishing tool which rotate around corresponding rotating axes, a workpiece holder for holding a workpiece which forms the dental prosthesis, and a base supporting the first and second spindles and the workpiece holder. The first and second spindles may be placed on the same axis (the first axis) in such a way as to face each other, the workpiece holder may move on a second axis intersecting the first axis and a third axis perpendicular to the first and second axes such that the workpiece held by the workpiece holder is placed between the first and second spindles, and the workpiece may be machined by alternately using the roughing tool and the finishing tool according to accuracy which is required when the workpiece held by the workpiece holder is machined.

That is, the first spindle and the second spindle may move on the first axis, and the workpiece holder may move on the second axis and the third axis, thus machining the workpiece three-dimensionally. Each spindle may be provided with the roughing tool and the finishing tool, so that the roughing tool alternates with the finishing tool when precision machining work is required.

Further, the first and second spindles may move on the first axis, and the workpiece holder may move on the second axis and the third axis which is perpendicular to the first and second axes while rotating around the second axis.

The rotating structure of the workpiece holder permits the easy machining of a portion which is difficult to be machined when the workpiece is machined by the movement of the spindles and the workpiece holder relative to the first, second and third axes.

The alternation of the roughing tool and the finishing tool may be performed through various constructions. Either of the roughing tool and the finishing tool may be located at a position at which the workpiece can be machined, and the roughing tool may alternates with the finishing tool by rotating each of the spindles 180 degrees.

Further, the roughing tool may alternate with the finishing tool by moving the workpiece holder on the second axis such that the workpiece is displaced from a position between the roughing tools or the finishing tools to a position between the finishing tools or the roughing tools.

The two roughing tools may be provided on the first and second spindles in such a way that they face each other and rotating axes thereof are not aligned with each other, and the two finishing tools may be provided on the first and second spindles in such a way that they face each other and rotating axes thereof are not aligned with each other. That is, if the rotating axes are aligned with each other, pressure acting on the workpiece is large, so that the workpiece may be undesirably broken or damaged. Especially when a thin part is machined, the possibility of damage increases. For the reasons, the rotating axes of the roughing tools or finishing tools are configured such that they are not aligned with each other, thus preventing the damage to the workpiece.

According to another aspect of the present invention, a rapid prototyping printer using three-dimensional printing technology is used as the dental prosthesis manufacturing machine. The three-dimensional printing technology is intended to rapidly manufacture a three-dimensional structure by layering conventional two-dimensional printing technology in stages. The rapid prototyping printer receives manufacturing data which is converted at the fifth step, thus shaping the cross-sections of respective layers and layering them, therefore providing a dental prosthesis.

The rapid prototyping printer manufactures a dental prosthesis using any one of metal, synthetic resin and porcelain. Preferably, the dental prosthesis is manufactured through the method of forming a metal support (porcelain crown) using metal.

Advantageous Effects

According to the present invention, a dental prosthesis can be manufactured by converting photographed data and operating a prosthesis manufacturing machine without manual operation, thus reducing manufacturing period and cost, eliminating danger and contamination occurring at the step of manufacturing the dental prosthesis, and achieving a dental prosthesis of uniform and precise quality.

BEST MODE

Hereinafter, the preferred embodiment of the present invention will be described with reference to the accompanying drawings. However, since the embodiment aids in understanding the present invention, the scope of the present invention is not limited to the embodiment.

Figure 1:
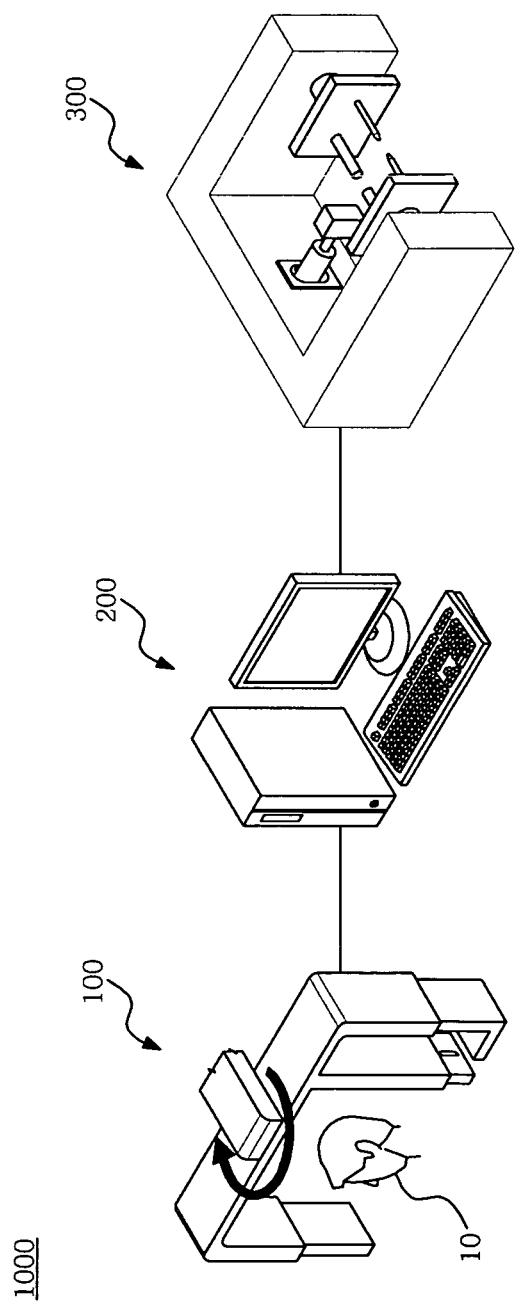
FIG. 1 is a schematic view illustrating devices used to perform the process of manufacturing a dental prosthesis according to an embodiment of the present invention.
Figure 2:
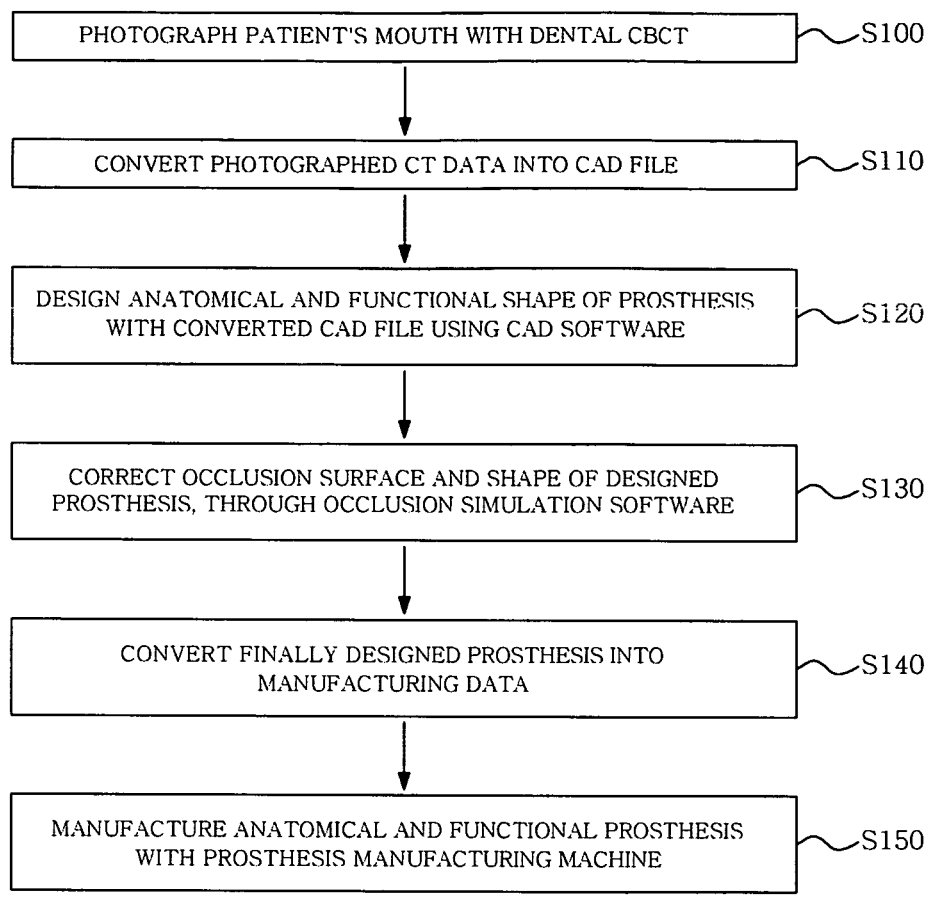
FIG. 2 is a flowchart illustrating the process of manufacturing a dental prosthesis according to an embodiment of the present invention.

FIG. 1 is a schematic view illustrating devices used to perform the process of manufacturing a dental prosthesis according to an embodiment of the present invention, and FIG. 2 is a flowchart illustrating the process of manufacturing a dental prosthesis according to an embodiment of the present invention.

Referring to FIGS. 1 and 2, the method of manufacturing the dental prosthesis includes the step S100 of photographing the mouth of a patient 10 using a dental cone beam CT (CBCT) 100. CT data which was photographed is transmitted to a computer 200. The computer 200 is provided with CAD software and occlusion simulation software, thus converting the CT data transmitted from the dental CBCT into a CAD file at step S110, and designing the anatomical and functional shape of the dental prosthesis with the CAD file using the CAD software at step S120. Thereafter, the designed shape of the prosthesis is corrected using the occlusion simulation software, at step S130. Next, the corrected design of the prosthesis is converted into prosthesis manufacturing data which can be recognized by a dental prosthesis manufacturing machine 300, at step S140. The manufacturing data is transmitted to the dental prosthesis manufacturing machine 300. The dental prosthesis manufacturing machine 300 manufactures a dental prosthesis using the manufacturing data, at step S150.

After the outer surface of the dental prosthesis manufactured through the above method goes through a planning process and a sterilizing and washing process, the dental prosthesis is put in the patient's mouth, thus appropriately supporting the inter-dental papilla or gingiva.

Figure 3:
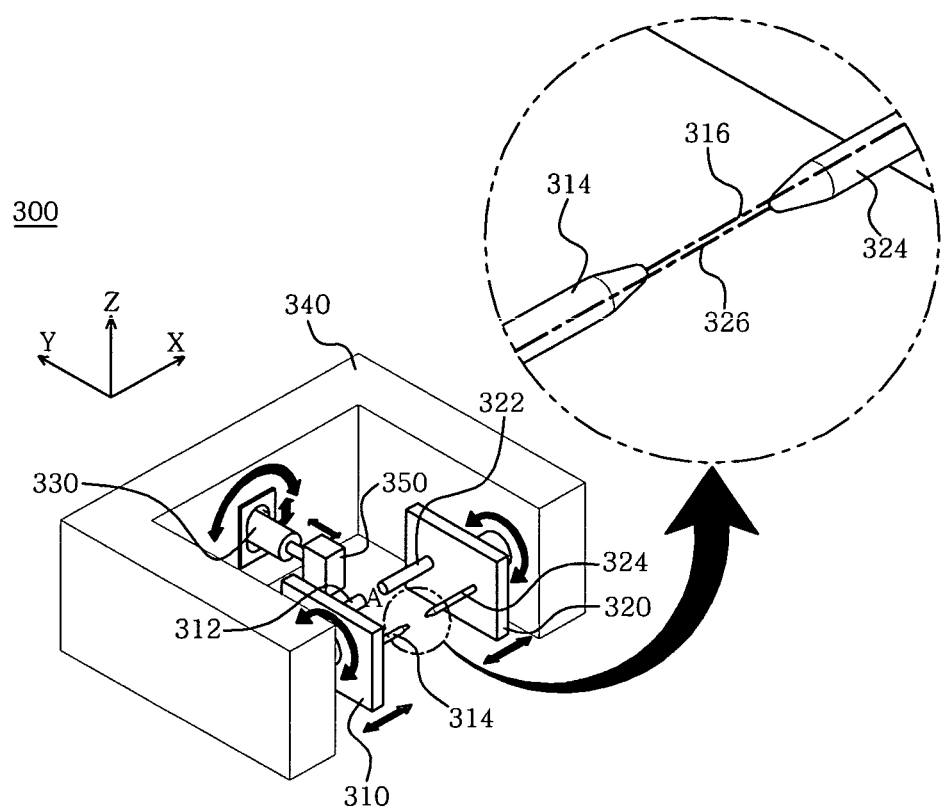
FIG. 3 is a schematic view illustrating the construction of a dental prosthesis manufacturing machine.

FIG. 3 is a schematic view illustrating the construction of a dental prosthesis manufacturing machine.

Referring to FIG. 3, the dental prosthesis manufacturing machine 300 includes a first spindle 310 equipped with a roughing tool 312 and a finishing tool 314, a second spindle 320 equipped with a roughing tool 322 and a finishing tool 324, a workpiece holder 330 for holding a workpiece 350, and a base 340.

Each of the roughing tools 312 and 322 and the finishing tools 314 and 324 rotates around its rotating axis to machine the workpiece 350. A drive motor is installed in each of the first and second spindles 310 and 320 to supply power for rotating the roughing tools 312 and 322 and the finishing tools 314 and 324.

In order to machine the workpiece three-dimensionally, the first spindle 310 and the second spindle 320 move on a first axis (X-axis), and the workpiece holder 330 moves on a second axis (Y-axis) and a third axis (Z-axis) while rotating around the second axis (Y-axis).

When the workpiece 350 is machined to manufacture the dental prosthesis, first, the workpiece 350 is located at a portion A and machined using the roughing tools 312 and 322. Afterwards, each of the first and second spindles 310 and 320 rotates 180 degrees, so that the finishing tools 314 and 324 are located at the portion A. Thereby, work which requires a high degree of accuracy and is difficult to be performed with the roughing tools 312 and 322 is conducted using the finishing tools 314 and 324.

The two finishing tools 314 and 324 which are coupled to the first and second spindles 310 and 320, respectively, in such a way as to face each other are configured so that the rotating axes 316 and 326 of the finishing tools 314 and 324 are not aligned with each other. The enlarged portion of FIG. 3 shows only the finishing tools 314 and 324. The configuration wherein rotating axes are not aligned with each other is identically applied to the two roughing tools 312 and 322.

The workpiece may be secured to the workpiece holder through various holding structures. For example, the following structures may be used.

That is, a polygonal hole may be formed in the workpiece holder 330, and a polygonal bar may be provided on the workpiece, so that the bar of the workpiece is inserted into the polygonal hole of the workpiece holder, and thus the workpiece is secured to the workpiece holder.

As another holding structure, the workpiece holder 330 may be made of shape memory alloy, and the workpiece may be provided with a bar, so that the workpiece holder tightens the bar of the workpiece at normal temperature, and loosens the bar of the workpiece at a predetermined range of temperature.

The bar of the workpiece secured to the workpiece holder is removed at the finishing step of the process.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

As described above, the present invention provides a method for manufacturing a dental prosthesis, using a prosthesis manufacturing machine which is constructed to machine a workpiece by alternately using a roughing tool and a finishing tool according to the accuracy required when the workpiece is machined. The method for manufacturing dental prosthesis according to the present invention is applicable in the dental field, and allows the dental prosthesis to be more efficiently and accurately manufactured.

The invention claimed is:

1. A method for manufacturing a dental prosthesis, comprising:
    a first step of photographing a mouth with a dental cone beam CT;
    a second step of converting CT data photographed at the first step into a CAD file;
    a third step of designing a shape of the dental prosthesis with the CAD file using CAD software;
    a fourth step of correcting the shape of the designed dental prosthesis using occlusion simulation software;
    a fifth step of converting the shape of the dental prosthesis which is designed finally into manufacturing data; and
    a sixth step of transmitting the manufacturing data to a dental prosthesis manufacturing machine, thus manufacturing the dental prosthesis,
    wherein the dental prosthesis manufacturing machine comprises:
    first and second spindles each having a roughing tool and a finishing tool which rotate around corresponding rotating axes;
    a workpiece holder for holding a workpiece which forms the dental prosthesis; and
    a base supporting the first and second spindles and the workpiece holder,
    wherein the first and second spindles are placed on the same axis, a first axis, in such a way as to face each other, the workpiece holder moves on a second axis intersecting the first axis and a third axis perpendicular to the first and second axes such that the workpiece held by the workpiece holder is placed between the first and second spindles, and the workpiece is machined by alternately using the roughing tool and the finishing tool according to accuracy which is required when the workpiece held by the workpiece holder is machined,
    wherein the first and second spindles move on the first axis, and the workpiece holder moves on the second axis and the third axis which is perpendicular to the first and second axes while rotating around the second axis.

2. The method according to claim 1, wherein the roughing tool alternates with the finishing tool such that either of the roughing tool and the finishing tool is located at a position at which the workpiece can be machined, and the roughing tool alternates with the finishing tool by rotating each of the spindles 180 degrees.

3. The method according to claim 1, wherein the roughing tool alternates with the finishing tool by moving the workpiece holder on the second axis such that the workpiece is displaced from a position between the roughing tools or the finishing tools to a position between the finishing tools or the roughing tools.

4. The method according to claim 1, wherein the two roughing tools are provided on the first and second spindles in such a way that they face each other and rotating axes thereof are not aligned with each other, and the two finishing tools are provided on the first and second spindles in such a way that they face each other and rotating axes thereof are not aligned with each other.

5. The method according to claim 1, wherein a polygonal hole is formed in the workpiece holder, and a polygonal bar is provided on the workpiece to be inserted into the polygonal hole of the workpiece holder.

6. The method according to claim 1, wherein the workpiece holder is made of a shape memory alloy, and the bar is provided on the workpiece to be secured to the workpiece holder.

* * * * *